(12) United States Patent
Braido et al.

(10) Patent No.: US 9,226,820 B2
(45) Date of Patent: Jan. 5, 2016

(54) AXIALLY ANCHORING COLLAPSIBLE AND RE-EXPANDABLE PROSTHETIC HEART VALVES FOR VARIOUS DISEASE STATES

(75) Inventors: Peter N. Braido, Wyoming, MN (US); Julia A. Neuman, Minneapolis, MN (US); Thomas M. Benson, Minneapolis, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 1096 days.

(21) Appl. No.: 12/737,254

(22) PCT Filed: Jul. 15, 2009

(86) PCT No.: PCT/US2009/004095
§ 371 (c)(1),
(2), (4) Date: Dec. 22, 2010

(87) PCT Pub. No.: WO2010/008549
PCT Pub. Date: Jan. 21, 2010

(65) Prior Publication Data
US 2011/0098800 A1    Apr. 28, 2011

Related U.S. Application Data

(60) Provisional application No. 61/135,076, filed on Jul. 15, 2008.

(51) Int. Cl.
*A61F 2/06* (2013.01)
*A61F 2/24* (2006.01)

(52) U.S. Cl.
CPC .............. *A61F 2/2412* (2013.01); *A61F 2/2418* (2013.01); *A61F 2220/0016* (2013.01); *A61F 2220/0075* (2013.01); *A61F 2230/008* (2013.01); *A61F 2230/0054* (2013.01)

(58) Field of Classification Search
CPC ............. A61F 2/915; A61F 2/89; A61F 2/91; A61F 2/82
USPC ....................... 623/1.12, 1.15, 1.16, 2.1, 2.14, 623/2.17–2.19
See application file for complete search history.

(56) References Cited

U.S. PATENT DOCUMENTS 7,018,406 B2   3/2006  Seguin et al.
7,198,646 B2   4/2007  Figulla et al.
(Continued)

FOREIGN PATENT DOCUMENTS

DE    202007005491 U1   6/2007
WO       03003949 A2    1/2003
(Continued)

OTHER PUBLICATIONS

International Search Report for Application No. PCT/US2009/004095 dated Oct. 21, 2009.
(Continued)

*Primary Examiner* — Yashita Sharma
*Assistant Examiner* — Tiffany Shipmon
(74) *Attorney, Agent, or Firm* — Lerner, David, Littenberg, Krumholz & Mentlik, LLP

(57) ABSTRACT

A stent (10) for use in a prosthetic heart valve has an annulus section (12) adapted for placement within the ' leaflets and annulus of the native heart valve. The annulus section has latch members (50) adapted to engage the leaflets of the native heart valve when prosthetic valve is implanted in the native valve. The latch members may hold the leaflets in engagement with the annulus section, and help to retain the prosthetic valve in position. The annulus section may have a non-circular cross-sectional shape.

25 Claims, 20 Drawing Sheets

(56) References Cited

U.S. PATENT DOCUMENTS

| | | | |
|---|---|---|---|
| 7,201,772 B2 | 4/2007 | Schwammenthal et al. | |
| 7,399,315 B2 | 7/2008 | Iobbi | |
| 7,429,269 B2 | 9/2008 | Schwammenthal et al. | |
| 2003/0097172 A1* | 5/2003 | Shalev et al. | 623/1.31 |
| 2004/0049262 A1 | 3/2004 | Obermiller et al. | |
| 2005/0096736 A1 | 5/2005 | Osse et al. | |
| 2005/0137690 A1 | 6/2005 | Salahieh et al. | |
| 2005/0137698 A1 | 6/2005 | Salahieh et al. | |
| 2006/0149360 A1 | 7/2006 | Schwammenthal et al. | |
| 2006/0178740 A1 | 8/2006 | Stacchino et al. | |
| 2006/0253191 A1 | 11/2006 | Salahieh et al. | |
| 2008/0071361 A1* | 3/2008 | Tuval et al. | 623/2.1 |
| 2008/0082166 A1 | 4/2008 | Styrc et al. | |
| 2009/0005863 A1 | 1/2009 | Goetz et al. | |
| 2009/0062908 A1 | 3/2009 | Bonhoeffer et al. | |

FOREIGN PATENT DOCUMENTS

| | | |
|---|---|---|
| WO | 2005002466 A2 | 1/2005 |
| WO | 2006127765 A1 | 11/2006 |
| WO | 2009045334 A1 | 4/2009 |
| WO | 2009053497 A1 | 4/2009 |

OTHER PUBLICATIONS

International Preliminary Report on Patentability for Application No. PCT/US2009/004095 dated Jan. 18, 2011.

* cited by examiner

200

300

300

AXIALLY ANCHORING COLLAPSIBLE AND RE-EXPANDABLE PROSTHETIC HEART VALVES FOR VARIOUS DISEASE STATES

CROSS-REFERENCE TO RELATED APPLICATIONS

This application claims the benefit of the filing date of U.S. Provisional Patent Application No. 61/135,076 filed Jul. 15, 2008, the disclosure of which is hereby incorporated herein by reference.

FIELD OF THE INVENTION

The present invention is directed to prosthetic heart valves for replacement of native heart valves, to stents for use in such prosthetic heart valves, and to methods of treating patients with such prosthetic heart valves.

BACKGROUND OF THE INVENTION

Certain prosthetic heart valves incorporate an expandable stent body and valve elements such as prosthetic valve leaflets mounted to the stent body. Valves of this type may be implanted in the heart by advancing the valve into the body of the patient with the stent body in a collapsed condition in which the stent body has a relatively small diameter. Once the valve is positioned at the desired implantation site, the stent body is brought to an expanded condition in which the stent body bears on the surrounding native tissue and holds the valve in place. The valve acts as a functional replacement for the diseased native valve. Thus, the valve elements inside the stent body permit blood flow in the antegrade direction but substantially block flow in the opposite, retrograde direction. For example, a prosthetic valve may be advanced to a site within a diseased native aortic valve percutaneously through the arterial system and into the aorta to the native aortic valve. In a transapical placement, a prosthetic valve may be advanced through an incision in the apex of the heart and through the left ventricle to the native aortic valve. Other approaches through other access sites can be used. Once the prosthetic valve is in place, it permits flow from the left ventricle into the aorta when the left ventricle contracts during systole, but substantially blocks retrograde flow from the aorta into the left ventricle during diastole.

There are significant challenges in design of an expandable stent body and valve. For example, the stent body desirably can be collapsed to a relatively small diameter to facilitate advancement into the body. However, the stent body must be capable of expanding to an operative, expanded condition in which the stent body securely engages the surrounding native tissues to hold the valve in place. The valve should form a good seal with the surrounding native tissues to prevent leakage around the outside of the prosthetic valve, commonly referred to as perivalvular leakage. The stent body, in its expanded, operative condition, desirably does not apply excessive forces to the annulus of the native valve. Excessive forces on the annulus of the native aortic valve can disrupt the electrical conduction system of the heart and also can impair the functioning of the mitral valve. These issues are complicated by the fact that the native valve leaflets ordinarily are left in place when an expandable prosthetic valve is implanted. The diseased native valve leaflets and other diseased tissues may present an implantation site which is irregular. For example, patients with calcified or stenotic aortic valves may not be treated well with the current collapsible valve designs, and may encounter problems such as (1) perivalvular leakage (PV leak), (2) valve migration, (3) mitral valve impingement, (4) conduction system disruption, etc., all of which can lead to adverse clinical outcomes. To reduce these adverse events, the optimal valve would seal and anchor adequately without the need for excessive radial force that could harm nearby anatomy and physiology.

Numerous prosthetic valve and stent body designs have been proposed. However, despite all of the attention devoted to such designs, still further improvements would be desirable.

BRIEF SUMMARY OF THE INVENTION

One aspect of the present invention provides a stent for use with a prosthetic heart valve for replacement of a native heart valve. The stent according to this aspect of the invention desirably includes an expandable non-woven stent body having a collapsed configuration and an expanded configuration. The stent body preferably includes an annulus section comprising at least one row of expandable cells. In the expanded configuration, the annulus section desirably is generally tubular and is adapted to engage the leaflets of the native heart valve and the annulus of the native heart valve so that a proximal end of the annulus section is disposed adjacent the annulus of the native valve and a distal end of the annulus section is disposed adjacent distal ends of the native leaflets. The stent body most preferably includes at least one latch member formed integrally with the annulus section. Each latch member preferably is connected to the annulus section at connection locations adjacent the distal end of the annulus section. Each latch member preferably has an engagement portion which is disposed outwardly of the distal end of the annulus section in the expanded configuration of the stent body. At least one leaflet of the native valve may be engaged by the engagement portion of at least one latch member and by the annulus section. As further explained below, the engagement of the latch members with the native valve leaflets can help to lock the stent body, and hence the valve as a whole in place, and can aid in effective sealing of the prosthetic valve with the native valve structure.

In certain embodiments, each latch member includes a pair of connection struts projecting from circumferentially-spaced locations on the annulus section, and the connection struts have distal ends distal to the annulus section. Each latch member may also include a pair of engagement struts connected to the connection struts adjacent the distal ends thereof and projecting proximally from their connections to the connection struts. The engagement struts of each latch member may be connected to one another adjacent proximal ends thereof. The engagement portion of each latch member may include the engagement struts. The expandable cells constituting the annulus section may include a plurality of interconnected cell struts joining one another at crests and defining the cells, the crests including a distal row of crests at the distal end of the annulus section. The connection struts may be connected to crests of the distal row. As discussed in greater detail below, this construction provides collapsible latch members which can be incorporated in the expandable stent body without adversely affecting its ability to collapse to a relatively small diameter.

A further aspect of the present invention also provides a stent for use with a prosthetic heart valve for replacement of a native aortic valve. The stent according to this aspect of the invention desirably includes an expandable stent body having an expanded configuration. In the expanded configuration, the stent desirably includes a generally tubular annulus section extending in proximal and distal directions, a generally tubular aorta section of larger diameter than the annulus section, the aorta section being spaced distally from the annulus section, and a plurality of support struts spaced circumferentially from one another interconnecting the annulus section with said aorta section. The stent body according to this aspect of the invention desirably includes at least one latch member connected to the stent body adjacent the annulus section and having an engagement portion disposed outward of the annulus section when the stent is in the expanded configuration. The stent body desirably is adapted for disposition with the annulus section adjacent the annulus of the native valve and at least partially within the leaflets of the native heart valve, the aortic section adjacent the native sinotubular junction and the support struts extending at least partially across the native Valsalva sinus, and with the at least one latch member engaged with at least one native valve leaflet so that each such native valve leaflet is engaged between the latch member and the annulus section.

A stent according to a further aspect of the invention desirably includes an expandable stent body having an expanded configuration including an annulus section having a plurality of cells cooperatively defining a generally tubular wall extending circumferentially around a proximal-to-distal axis. The wall may have a scalloped distal edge including a plurality of circumferentially-spaced recess regions and a plurality of circumferentially spaced projections extending distally beyond the recess regions, the projections being interspersed with the recess regions around the circumference of the tubular wall. As further discussed below, a stent according to this aspect of the invention may be implanted with the projections confronting the native valve leaflets so that the projections help to hold the native valve leaflets in place. A stent according to this aspect of the invention may be provided with latch members as discussed above.

Still further aspects of the invention provide valves with stents as aforesaid and with flexible prosthetic valve leaflets mounted in the stents. Additional aspects of the invention provide methods of treatment including implanting the valves within the body of a patient.

Yet another aspect of the invention provides a prosthetic heart valve for replacement of a native valve. The valve according to this embodiment of the invention desirably includes a stent body having a structure extending circumferentially around a proximal-to-distal axis, the structure having a region with a non-circular cross-section in a plane perpendicular to the proximal-to-distal axis, and three prosthetic valve leaflets. The prosthetic leaflets have free edges and are adapted to coapt with one another at the free edges. The free edges of the leaflets may be connected to the structure within said region at commissure locations circumferentially spaced around the proximal-to-distal axis. For example, the non-circular cross-section may be elliptical or triangular. In an implantation method according to a further aspect of the invention, a valve with a triangular cross-section may be implanted in diseased native valve having three leaflets with side regions of the stent body facing the native valve leaflets.

BRIEF DESCRIPTION OF THE DRAWINGS

FIG. 30 is a an end view of the leaflet assembly shown in FIG. 29;

DETAILED DESCRIPTION

Figure 1:
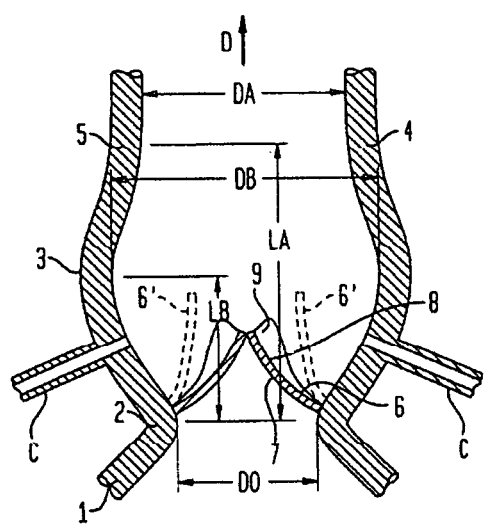
FIG. 1 is a schematic sectional view of the aortic root tissue in a typical human heart.

FIG. 1 is a simplified view of the geometry or anatomy of the aortic root tissue in a typical human heart. The left ventricular outflow tract (LVOT) 1 communicates with the ascending aorta 5 through the annulus 2 of the native aortic valve and the Valsalva sinus 3. The sinus joins the aorta at the sinotubular junction (STJ) 4. The native aortic valve typically includes three native valve leaflets 6, of which only two are visible in FIG. 1. As the left ventricle contracts during systole, blood is forced from the LVOT 1 through the native valve and sinus and into the aorta 5, moving generally in the downstream or antegrade flow direction indicated by arrow D. In a healthy individual, the native valve leaflets 6 open away from one another and move to the position schematically shown in broken lines at 6' to permit flow in this direction. During diastole, when the ventricle is not contracting, the native valve leaflets 6 move back to the position indicated in solid lines in FIG. 1, where they abut one another or "coapt" so as to substantially block flow in the upstream or retrograde direction, opposite to arrow D. The direction "distal" as used herein with reference to a feature of the native circulatory system refers to the direction of antegrade flow, i.e., the predominant direction of blood flow through such feature, as indicated by arrow D. The direction "proximal" as used herein with reference to a feature of the native circulatory system is the opposite direction.

The parameters identified in FIG. 1 are as follows: DO=orifice diameter, i.e., the interior diameter of native annulus 2; DA=the diameter of the aorta just distal to the sinus; DB=maximum projected sinus diameter (this sinus is sometimes known as the Valsalva sinus); LA=length of the sinus, i.e., the dimension in the distal direction from the annulus 2 to the sinotubular junction 4; and LB=distance in the distal direction between DO and DB.

The leaflets 6 have distal edges 9 remote from the annulus 2. Each native leaflet 6 has a surface 7, referred to herein as the "interior" surface of the leaflet, facing generally towards the other leaflets. Each native leaflet 6 also has a surface 8, referred to herein as the "exterior" surface of the leaflet, facing outwardly, away from the other leaflets and toward the wall of the sinus 3. The cross sectional shape of such a native valve varies somewhat from individual to individual, and this variation can be increased by various types of disease. For example, disease can reshape the cross section of a patient's valve to a circular, triangular, or elliptical shape, depending on the disease state.

An expandable stent body 10 (FIGS. 2 and 3) for a collapsible/expandable prosthetic heart valve in accordance with one embodiment of the present invention is formed as a unitary structure as, for example, by laser cutting or etching a tube of a superelastic metal alloy such as a nickel-titanium alloy of the type sold under the designation NITINOL. Such a unitary structure can also be referred to as a "non-woven" structure, in that it is not formed by weaving or winding one or more filaments. In its fully-expanded, unconstrained configuration (FIG. 3), stent body 10 includes an annulus section 12, an aorta section 20 and support struts 30 extending between the annulus section and the aorta section. The annulus section 12 in the expanded configuration is generally in the form of a cylindrical tube having a central axis 14, whereas aorta section 20 is generally in the form of a hoop coaxial with the annulus section.

Figure 5:
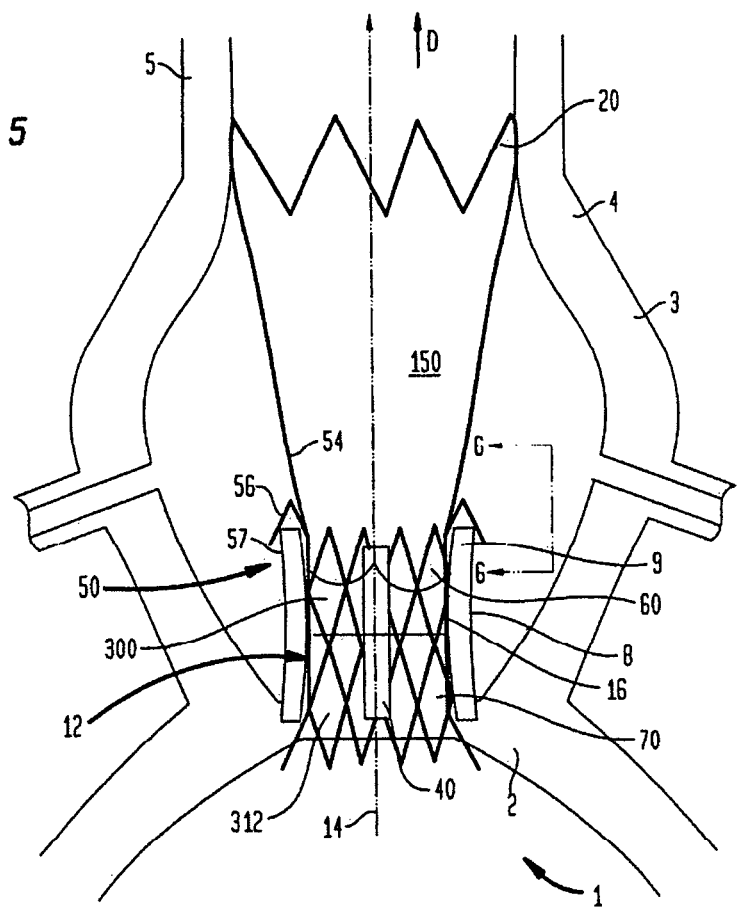
FIG. 5 is a schematic sectional view of a portion of a valve incorporating the stent of FIGS. 1-4 in conjunction with the aortic root.

As best seen in FIG. 5, the stent body is adapted for installation in the body of a patient with the annulus section adjacent the annulus 2 and with the aorta section 20 adjacent the sinotubular junction 4 and aorta 5. Thus, when the valve incorporating the stent body is placed in the patient, the aorta section 20 will be disposed distal to the annulus section 12 in the frame of reference of the patient's circulatory system. Accordingly, as used with reference to features of the stent body and valve, the direction D (FIGS. 3 and 5) along axis 14 from the annulus section 12 towards the aorta section 20 is referred to as the distal direction, and the opposite direction is taken as the proximal direction. Stated another way, the distal direction along the stent body is the direction from the end of the stent which is intended for disposition at a proximal location in the frame of reference of the circulatory system to the end of the stent which is intended for disposition at a more distal location in the frame of reference of the circulatory system. Also, the outward direction as used with reference to the stent body is the direction away from the proximal-to-distal axis 14. The directions toward and away from axis 14 are also referred to herein as the "radial" directions. As used with reference to features of the stent body, the "circumferential" directions are the directions around axis 14.

Figure 2:
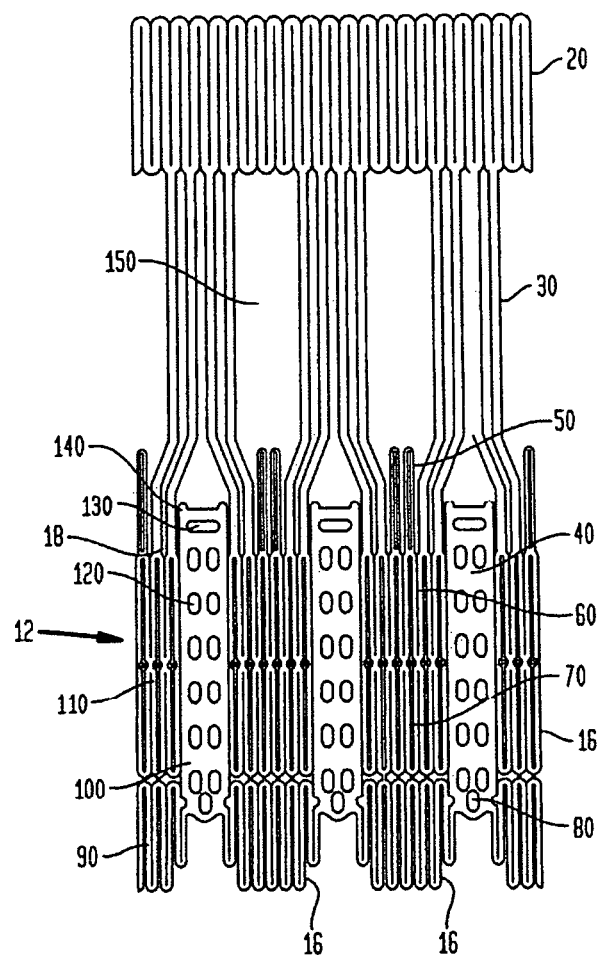
FIG. 2 is a developed view of a stent in accordance with one embodiment of the present invention in a collapsed configuration.
Figure 3:
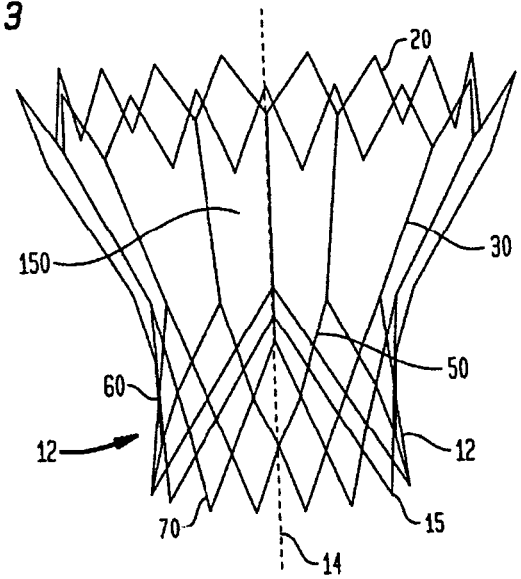
FIG. 3 is a perspective view of the stent shown in FIG. 2 in an expanded condition.

FIG. 2 shows the stent body 10 in a compressed condition, also referred to as the unexpanded condition, and depicts the stent in a developed view. In this view, the stent body is seen as though it has been cut along its length or proximal-to-distal extent (from top to bottom as viewed in FIG. 2) and laid out flat, with the circumferential direction extending to the left and right as seen in FIG. 2.

As best seen in FIGS. 2, 3, 5, and 6 the annulus section 12 includes numerous cells defined by interconnecting struts 16 which join one another at intersection points. These cells are disposed in a proximal row 70 and distal row 60, each such row extending circumferentially around the proximal-to-distal axis 14 so that the cells cooperatively form a generally cylindrical wall. In the expanded condition, the struts of each cell form a generally diamond-shaped structure. In the unexpanded or collapsed configuration, the struts of each cell extend substantially proximally and distally, so that each cell is collapsed in the circumferential direction. The intersection points 18 between the struts on the distal side of distal row 60 define the distal edge of the annulus section. These intersection points are referred to herein as the distal crests 18 of the annulus section.

The annulus section also includes a set of solid elements 40 referred to herein as commissure posts, formed integrally with the remainder of the stent body. The commissure posts extend proximally and distally at three locations spaced equally around the circumference of the annulus section. Each commissure post has rows of eyelets 120 extending proximally and distally along the post, and with a further eyelet 130 adjacent the distal end of the post. Each commissure post also has small axial projections or "ears" 140 at its distal end. Three prosthetic valve leaflets 300 (FIG. 5) are sutured to the posts, so that the leaflets are disposed within the annulus section 12 of the stent body. The sutures (not shown) may extend through the eyelets 120 and 130, and may also be engaged between the ears 140. A lining or "cuff" 312 may be provided on the interior surface, exterior surface or both of the annulus region, over all or part of the axial extent of the annulus region. The leaflets and cuff may be formed from conventional biocompatible materials such as synthetic polymers and animal tissues such as pericardial tissues.

The posts are connected to the struts 16 constituting the cells. As best seen in FIG. 2, the commissure posts are connected to the struts constituting the cells at connections 110 near the midpoints of the struts, and at further connections near the proximal ends of the struts and near the proximal end of the annulus section. At some of the intersection points 100 between struts 16 of the proximal cell row 70 adjacent the commissure posts 40, the struts disposed proximally to such intersection point are not connected to the struts disposed distally to the intersection point. This provides increased flexibility to the struts connected with the proximal ends of the commissure post. The connections between the commissure posts and the struts of the annulus region allow the posts to flex or tilt in the radial directions, towards and away from the axis 14 (FIG. 5), when the valve is in operation with the stent body in an expanded condition. The omitted connections at intersection points 100 also reduce the radial stiffness of the base region 90 of the stent body at the proximal end of the annulus section. This limits the radially outward force applied by the base region of the stent body to the surrounding native tissues at the proximal end of the annulus section. As also seen in FIG. 2, base region 90 of the stent can be scalloped (i.e., undulating proximally and distally as one proceeds in a circumferential direction around the stent) to more closely mimic or follow the true native annulus shape.

As best seen in FIG. 2, support struts 30 extend distally from some of the distal crests 18 at the distal edge of distal cells 60. The support struts 30 are not distributed evenly around the circumference of the annulus section. The support struts are arranged in groups, each such group being associated with one of the commissure posts 40 and connected to distal crests 18 adjacent to the associated commissure post. In the particular embodiment depicted, each group includes four support struts, with two on each side of the associated commissure post. This arrangement of the support struts provides gaps 150 between the groups of support struts. Stated another way, at least some of the distal crests 18 remote from the commissure posts are not connected to the support struts.

Aorta section 20 is formed by a set of struts which define a row or half-cells. The configuration of the struts and aorta section may be varied from that shown. For example, the aorta section may include one or more rows of full cells such as those constituting the annulus section. Also, the support struts may have a branched configuration, so that the distal end of each support strut is connected to plural points on the aorta section. More or fewer support struts may be provided.

Figure 6:
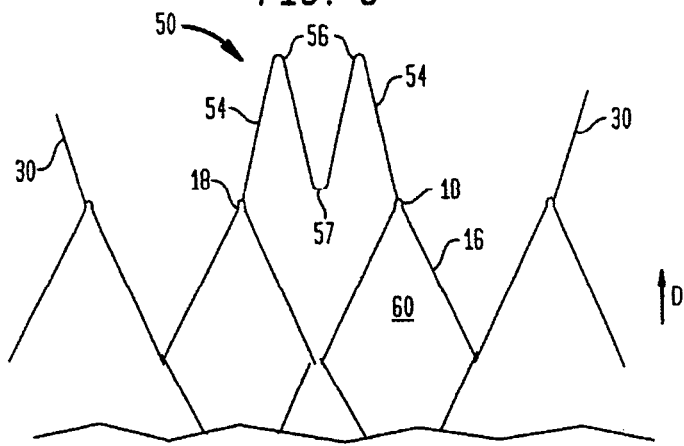
FIG. 6 is a fragmentary schematic elevational view taken along line 6-6 in FIG. 5, with certain features omitted for clarity of illustration.

The stent body also includes three latch members 50 formed integrally with the rest of the stent body. The latch members 50 are equally spaced from one another in the circumferential direction. The latch members are connected to distal crests 18 in the gaps 150 between the groups of support struts. As best seen in FIG. 6, each latch member includes a pair of connection struts 54 extending distally from two distal crests 18. Each latch member also includes a pair of engagement struts 56 extending generally proximally from the distal ends of the connection struts. In the expanded configuration depicted in FIG. 6, the distal ends of the connection struts 54 slope in circumferential directions toward one another, and the proximal ends of the engagement struts 56 slope toward one another and join one another at a proximal juncture 57 formed by a small arcuate proximal end member. In this expanded condition, the latch member as a whole is generally W-shaped, with the tips of the W-shape being connected to the distal crests 18 of the annulus section.

Figure 4:
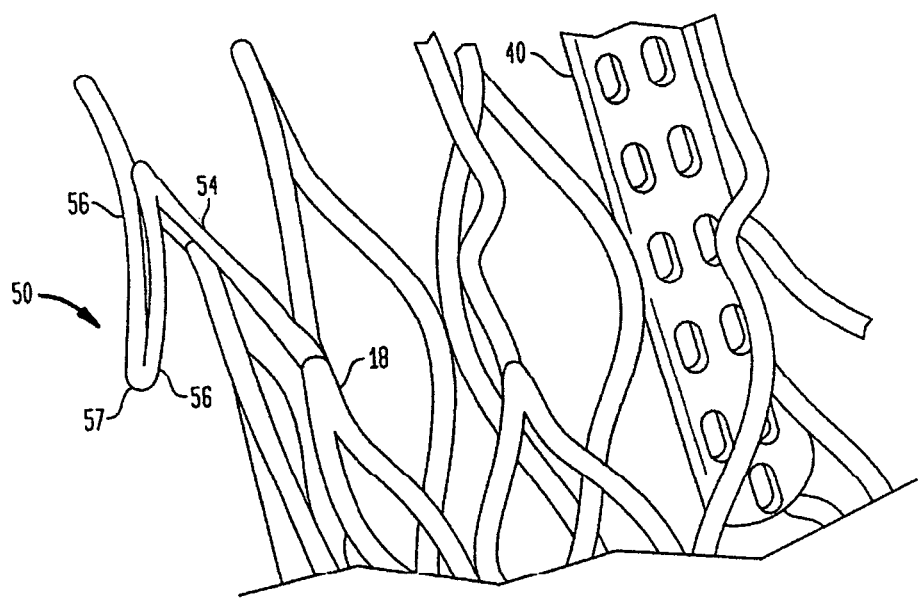
FIG. 4 is a fragmentary enlarged perspective view of a portion of the stent shown in FIG. 3.

In the expanded configuration of the stent body, the distal ends of the connection struts 54 slope radially outwardly, away from axis 14 (FIG. 5). Also in the expanded condition, the proximal ends of the engagement struts 56 slope radially outwardly, so that the proximal juncture 57 is disposed radially outward of the distal end of annulus section 12. The proximal juncture lies just distal to the distal end of the annulus section. See also FIG. 4, which is an enlargement of one representative latch member 50 in its expanded configuration.

The structure of the latch member allows it to collapse in the circumferential direction. Thus, in the collapsed configuration of the stent body depicted in FIG. 2, the connection struts 54 and engagement struts 56 extend substantially axially. The engagement elements 50 do not restrict the motion of crests 18 toward one another in the circumferential direction during collapse of the stent body. Also, because the engagement elements are disposed in the gaps 150 between support struts 30, they do not interfere with the support struts 30 during collapse. The engagement elements do not increase the collapsed diameter of the stent body.

The stent body may also include eyelets 80 that can be engaged with a delivery device during implantation of the prosthetic heart valve into the patient. Features such as this can be placed wherever needed on the stent body.

In operation, the valve is brought to a collapsed condition and mounted on a delivery device (not shown) such as an elongated probe having a sheath adapted to retain the stent body in the collapsed condition, and having provisions for moving the sheath relative to the stent body to release the stent body from the sheath. The delivery device is advanced into the patient's body until the valve is aligned with the native aortic valve, with the annulus section 12 adjacent the annulus of the aorta. The valve is released from the sheath and stent body 10 expands under its own resilience. The resilient expansion may occur solely as a result of release of mechanical constraint from the stent body, or may include expansion resulting from the effects of temperature change on the material of the stent body. Preferably, the entire expansion of the stent body from its collapsed condition to its expanded, operative condition is brought about by the stent body itself. Stated another way, the stent body desirably is fully self-expanding and does not require a balloon or mechanical movement device to bring about any part of the expansion. The annulus section 12 engages the annulus 2 of the native aortic valve, and also engages the interior surfaces 7 of the native valve leaflets. Each latch member 50 engages one of the native valve leaflets at or near the distal edge 9 of such native leaflet. The engagement struts 56 and proximal juncture 57 of each latch member 50 bear on the exterior surface 8 of the leaflet at or near the distal edge. Although the leaflets are shown as simple geometric shapes in FIG. 5 for ease of illustration, it should be appreciated that the leaflets typically have irregular shapes. For example, the leaflets may be nodular or rough. The aorta section 20 engages the native anatomy at or near the sinotubular junction 4.

Although the stent reaches an expanded configuration, it typically does not reach its fully-expanded, unconstrained configuration. Thus, the resilience of the stent body normally causes the aortic section 20 to bear on the sinotubular junction and also causes the annulus section 12 to bear on the annulus and on the interior surfaces of the leaflets. The prosthetic valve leaflets 300 open to allow distal or antegrade flow of blood during systole, and close to block proximal or retrograde flow during diastole. The engagement of the latch members 50 with the native valve leaflets helps to maintain the stent body, and hence the valve, in position. In particular, such engagement helps to prevent movement of the valve in the proximal or retrograde direction. Therefore, the resilient engagement between the annulus section 12 and aorta section 20 with the native anatomy need not provide all of the force necessary to resist such movement. Moreover, the engagement of the latch members with the native valve leaflets tends to bias the native leaflets inwardly toward the annulus section 12 of the stent body. This tends to improve sealing between the native leaflets and the stent body and cuff 312 (FIG. 5) and helps to resist perivalvular leakage or retrograde flow around the outside of the stent body. The latch members facilitate satisfactory valve action without the need for extremely high radial forces between the annulus section 12 of the stent body and the native valve anatomy. This is advantageous, inasmuch as excessive radial forces on the native anatomy may disrupt the electrical conduction system of the heart and or distort the mitral valve, which is disposed near the annulus of the aortic valve.

The resilience of the latch members allow them to attach to both calcified and non-calcified leaflets. For example, if a leaflet is thick, nodular or both, the engagement struts 56 of the latch member can be bent outwardly by the leaflet. In this condition, the latch member tends to push the leaflet inward against the annulus section of the stent body. The systolic blood pressure tends to force the native valve leaflets into engagement with the annulus section of the stent body. By retaining the native leaflets in position, the latch members facilitate this action.

The prosthetic valve allows antegrade flow into the aorta, and also allows flow into the Valsalva sinus and thus into the coronary arteries C which communicate with the sinus. The gaps or spaces 150 between posts 30 provide large openings for flow into the sinus. Moreover, engagement of the native valve leaflets by the latch members 50 may help to assure that the native valve leaflets do not block the openings of the coronary arteries.

The features discussed above can be varied. For example, size and shape of the latch members 50 can be selected to match the condition of the patient's native valve leaflets as measured, for example, by imaging techniques before or during the procedure. A kit including different valves with stent bodies having different latch members may be provided to facilitate such selection.

Figure 7:
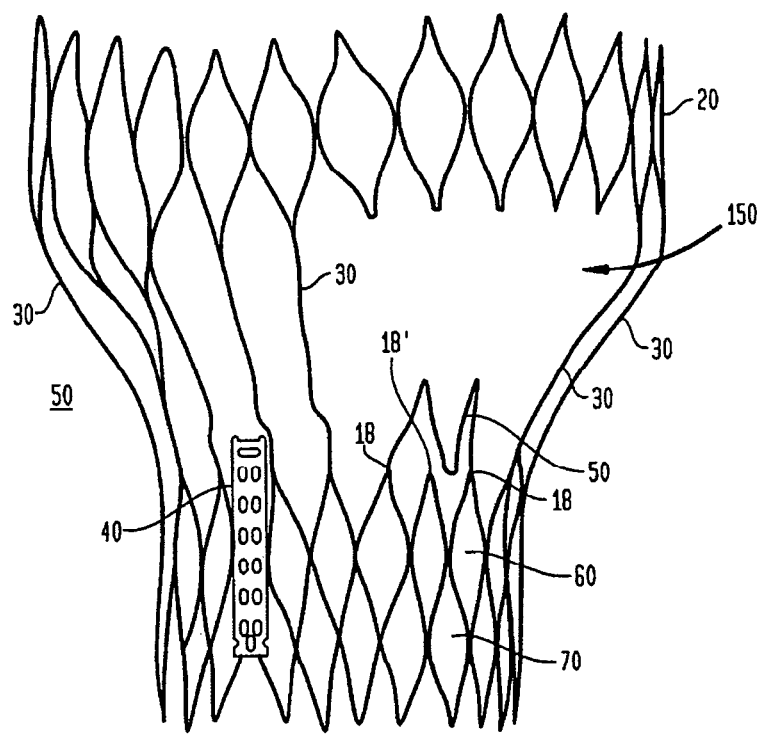
FIG. 7 is an elevational view of a portion of a stent in accordance with a further embodiment of the present invention.

The stent body may include more or fewer rows of cells in the annulus section. Also, the annulus section 12 and aorta section 20 need not be in the form of circular cylinders. For example, in a variant of the stent shown in FIGS. 2-6, annulus section 12 in its fully expanded, unconstrained configuration may be generally in the form of a cone or other surface of revolution about the proximal-to-distal axis 14. Where the annulus section is tapered and has a distal end of smaller diameter than the proximal end, the latch members may be arranged so that their engagement portions, such as the engagement struts 56 and proximal end member 57 are disposed outward of the distal end of the annulus but not outward of the proximal end of the annulus section. As further discussed below, the annulus section may not be in the form of a surface of revolution but instead may have a non-circular cross-sectional shape. Also, the aorta section may include one or more rows of complete cells. For example, FIG. 7 shows the foreground half of a fully expanded stent body 10. (The rear half is omitted to avoid over-complicating the drawing.) The FIG. 7 stent body is a tricuspid design, similar to the stent body discussed above, and has three latch members 50 120° apart. However, the aorta section 20 in the stent body of FIG. 7 includes full cells. FIG. 7 also shows how the distal portion 20 of the stent body 10 can be scalloped (or undulating as one proceeds in the circumferential direction around the stent) to conform to the anatomy. The latch members 50 incorporated in the stent body of FIG. 7 are similar to those discussed above, except that each latch member 50 in FIG. 7 is connected to two non-adjacent distal crests 18. Stated another way, the two distal crests 18 connected to each latch member 50 lie on opposite sides of a third distal crest 18'. Thus, each latch member 50 has a somewhat larger circumferential span than in the embodiments discussed above.

Figure 8:
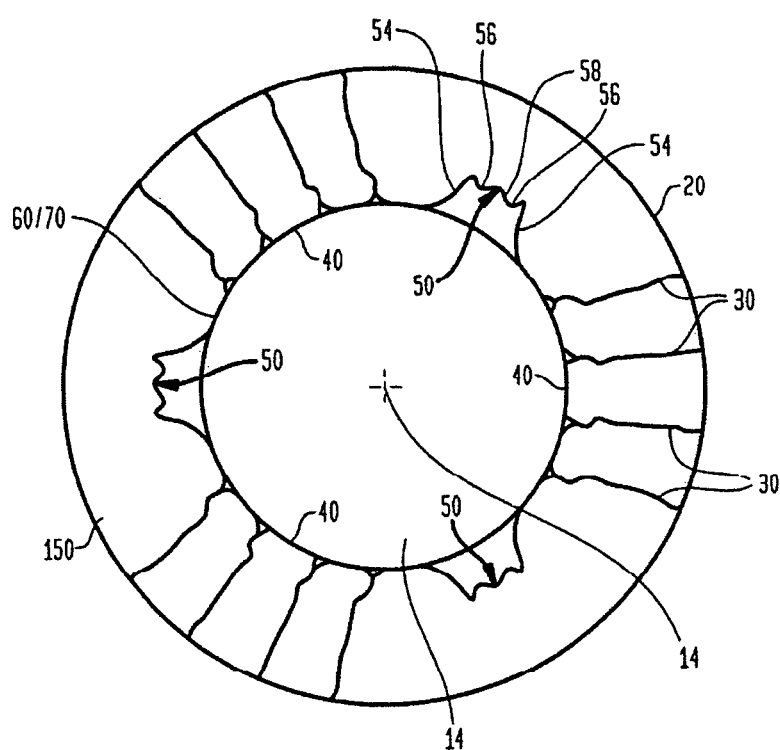
FIG. 8 is an end view of a stent according to another embodiment of the present invention.

A further stent body is seen in FIG. 8 in end view looking along the axis 14 of the body in an expanded condition. This stent body is also a tricuspid design, with three latch members 50 at 120° apart. Three commissure posts 40 are also spaced 120° apart. The annulus region cells 60 and 70, latches 50, and aorta section 20 are at progressively larger diameters to accommodate the patient's anatomy. In the stent body of FIG. 8, each latch member 50 has a proximal end member 59 extending between the proximal ends of the engagement struts 56.

Figure 9:
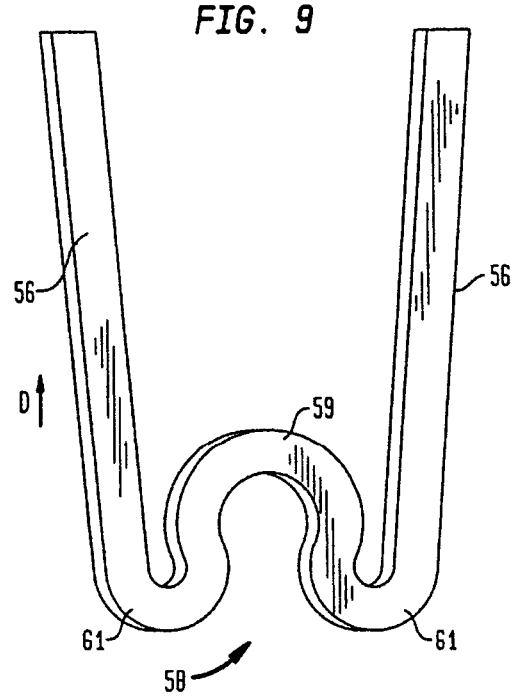
FIGS. 9, 10 and 11 are fragmentary views depicting portions of stents according to further embodiments of the invention.

As seen in detail in FIG. 9, a latch member according to a further embodiment also has a proximal end member 58 interconnecting the proximal ends of engagement struts 56. In this embodiment, the proximal end member is convoluted and includes a bend or bight 59 projecting in the distal direction D from the proximal ends of the engagement struts. Small curved sections 61 are provided at the junctures between bight 59 and the engagement struts. Here again, the distal ends of the engagement struts 56 are connected to connecting struts (not shown) which in turn are connected to the annulus region of the stent body as discussed above. The convoluted proximal end member provides additional resilience in the circumferential direction, and also can allow some local deformation in radial directions as the proximal ends of the engagement struts engage the native valve leaflet.

Figure 10:
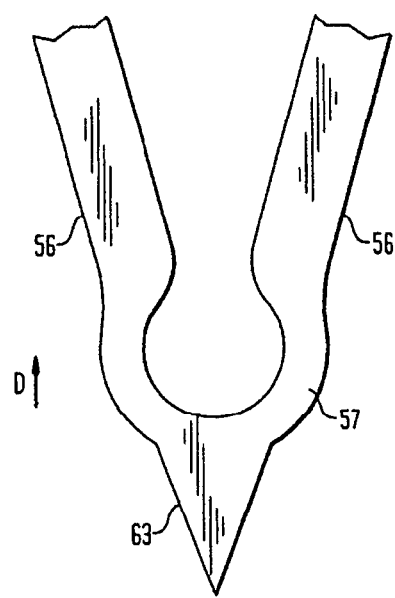

A further latch member (FIG. 10) has a curved proximal juncture 57 similar to the proximal juncture discussed above with reference to FIG. 6. However, the curved member forming juncture 57 has a width smaller than the width of the engagement struts 56, and hence has a smaller cross-sectional area than the engagement struts. Also, the proximal end juncture 57 of FIG. 10 has a pointed barb 63 projecting generally in the proximal direction. Such a barb can be engaged in the native tissue as, for example, in the native valve leaflet, to hold the native valve leaflet in position relative to the stent body. This provides an even more secure engagement between the stent body and the native valve leaflets, and thus provides even more secure anchorage of the valve. Barbs of this type can be provided on latch members of different configurations. Also, the juncture of reduced cross-sectional area can be used without a barb.

Figure 11:
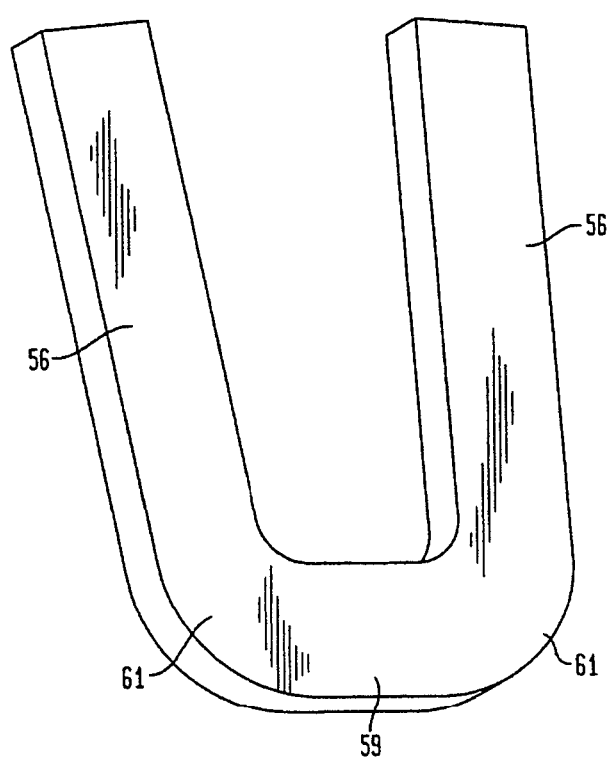

A latch member according to yet another embodiment (FIG. 11) has a substantially straight proximal end member 59 connecting the proximal ends of the engagement struts 56, and small curved sections 61 at the junctures between the proximal end member and the engagement struts.

Figure 12:
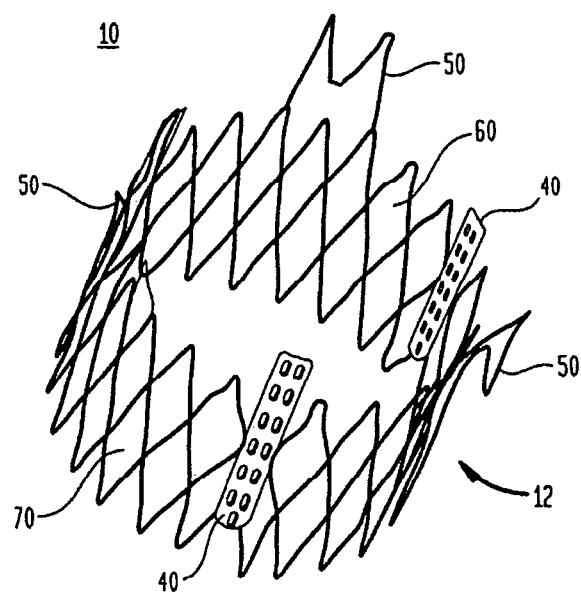
FIG. 12 is a perspective view of a stent in accordance with yet another embodiment of the present invention.
Figure 13:
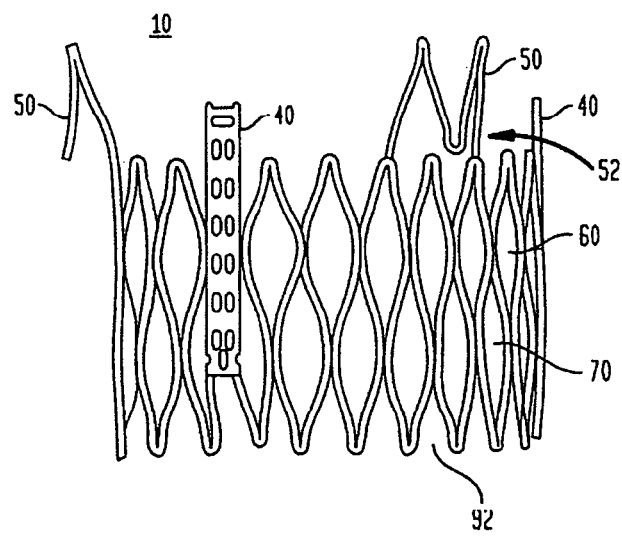
FIG. 13 is an elevational view of the stent shown in FIG. 12.

A stent body according to a further embodiment, depicted in FIGS. 12 and 13, is similar to the stent bodies discussed above, except that the aorta section and connecting struts are omitted. Here again, the stent body is incorporated in a tricuspid prosthetic valve, and hence includes attachments in the form of three commissure posts 40 disposed at 120° circumferential spacings for three prosthetic leaflets. The stent body incorporates three latch members 50 which are also disposed at 120° circumferential spacings. This design for stent body 10 has an annulus section 12, including rows of cells 60 and 70, that anchors within the patient's native heart valve leaflets and extends adjacent to or within the annulus of the native valve. The commissure posts are disposed in part within the axial extent of the annulus section, but project distally from the annulus section. Thus, the prosthetic valve leaflets (not shown) will be disposed in part within the annulus section, with portions of the leaflets extending distal to the annulus section. The latch members 50 may include any of the latch member features discussed above.

As best seen in FIG. 13, the base or proximal edge 92 of the annulus section is scalloped or undulating, so that it is curved in the distal direction adjacent each of commissure posts 40, and in the proximal direction between circumferentially adjacent commissure posts 40. A valve incorporating the stent body of FIGS. 12 and 13 may be installed, for example, in a native valve having three leaflets as, for example, in the aortic valve or in the native tricuspid valve which connects the right atrium with the right ventricle.

Figure 14:
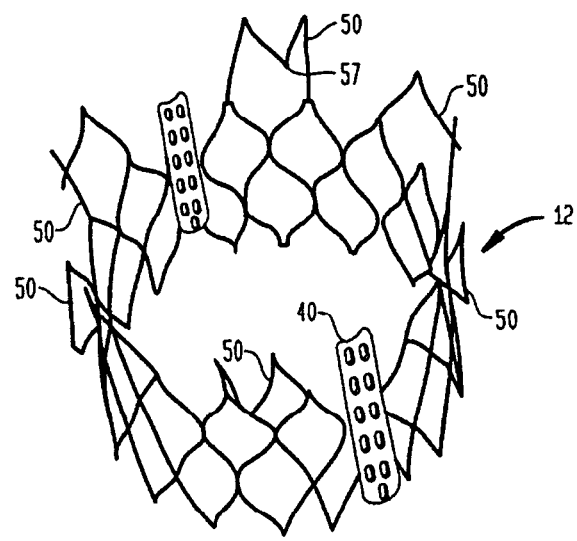
FIG. 14 is a perspective view of a stent in accordance with a further embodiment of the present invention.
Figure 15:
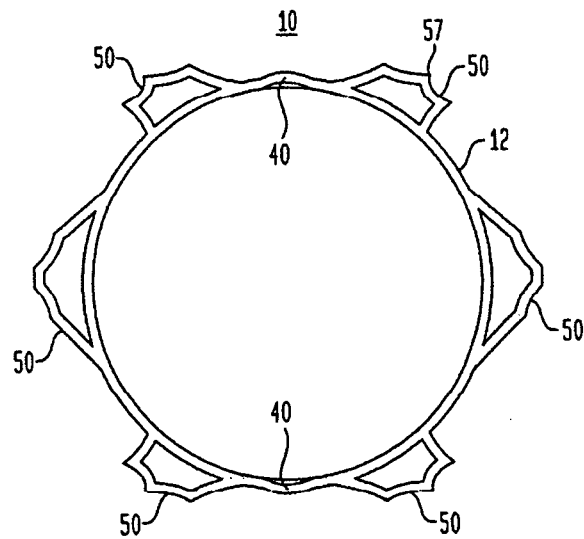
FIG. 15 is an end view of the stent shown in FIG. 14.

The stent body 10 of FIGS. 14 and 15 is generally similar to the stent body of FIGS. 12 and 13, in that the stent body includes only an annulus section and associated features. The stent body of FIGS. 14 and 15 incorporates only two commissure posts 40 for supporting two leaflets of a bicuspid prosthetic valve. Also, the stent body of FIGS. 14 and 15 incorporates six evenly spaced latch members 50. This stent body may be used, for example, in a bicuspid native valve as, for example, in the mitral valve. When this stent body is implanted, three of the latch members 50 engage each of the two native valve leaflets. It will be appreciated that any number of latch members and any spacing between latch members can be used. This design has sharper, more "barb-like" proximal end junctures 57 to the latches 50.

Figure 16:
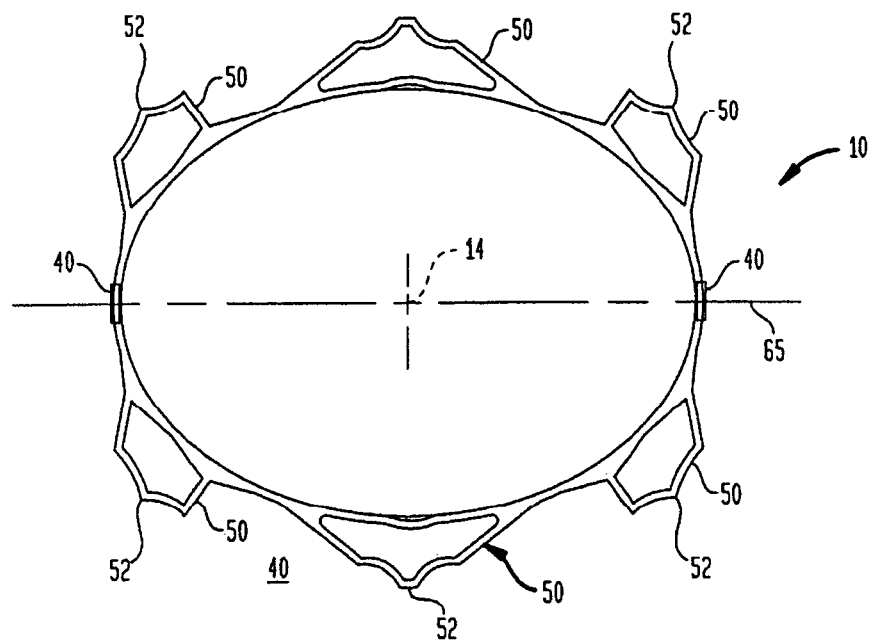
FIG. 16 is a perspective view of a portion of a stent in accordance with another embodiment of the present invention.

A stent body according to a further embodiment is seen in the FIG. 16 end view along the proximal-to-distal axis 14. Here again, the annulus section includes rows of cells which cooperatively define a generally tubular wall. However, in the fully expanded, unconstrained condition depicted, the tubular wall is generally elliptical in cross-section rather than circular in cross-section. The commissure posts 40 are disposed at circumferential positions on the long axis 65 of the elliptical cross-section. This stent is also intended for use in a bicuspid prosthetic valve. A valve incorporating a stent body of this type may be implanted in a native valve having a non-circular shape. For example, certain patients have native aortic valves which are bicuspid rather than tricuspid. A stenotic bicuspid aortic valve may define an opening which is generally elliptical in cross-section. The long axis 65 of the elliptical cross-section may be aligned with the long axis of the native valve opening. Also, a valve having an elliptical stent body can be implanted in the annulus of the native mitral valve.

Figure 17:
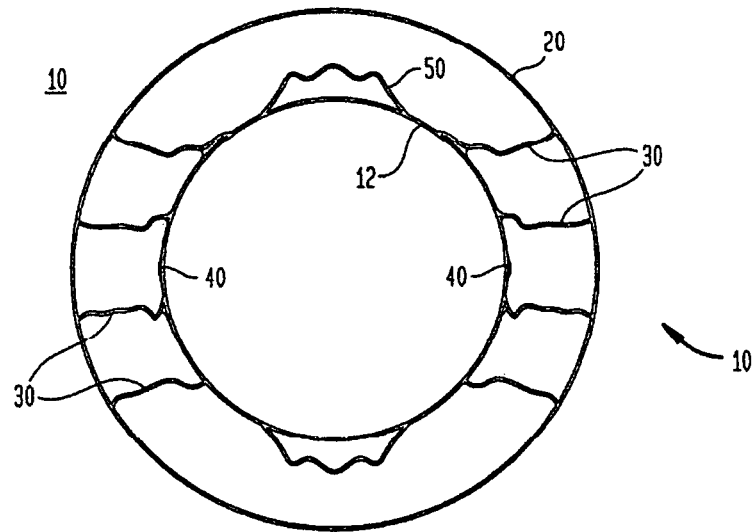
FIG. 17 is an end view of a stent in accordance with still another embodiment of the present invention.

FIG. 17 is an axial end view of a bicuspid design with two latches 50 spaced evenly around the circumference thereof, and with two leaflet (commissure) posts 40. This embodiment again includes a distal or aortic section 20 and support struts 30 connecting the annulus section 12 with the aortic section 20.

Figure 18:
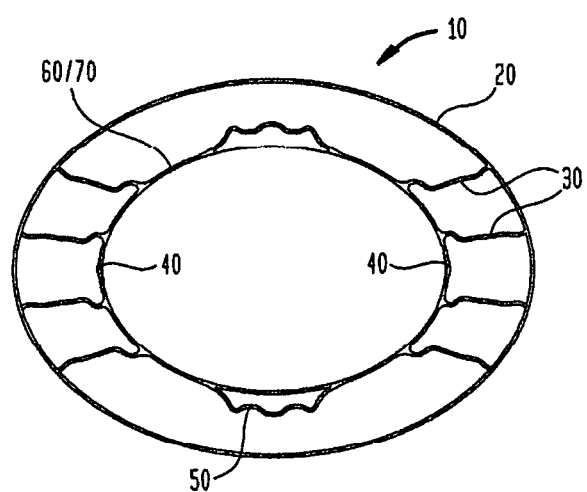
FIG. 18 is an end view of a stent in accordance with a further embodiment of the present invention.

FIG. 18 is a top view of a bicuspid design with two latches 50 spaced evenly around the circumference thereof, and with two leaflet (commissure) posts 40. This design illustrates that not only can the annulus section 12 have a shape which is other than circular (in this case, elliptical), but the distal or aorta section 20 can also be non-circular (again, in this case, elliptical). Another possibility (not shown) is a design in which the proximal or annulus section and the distal or aortic sections are not concentric, e.g., to allow for curvature variations in the ascending aorta.

Figure 19:
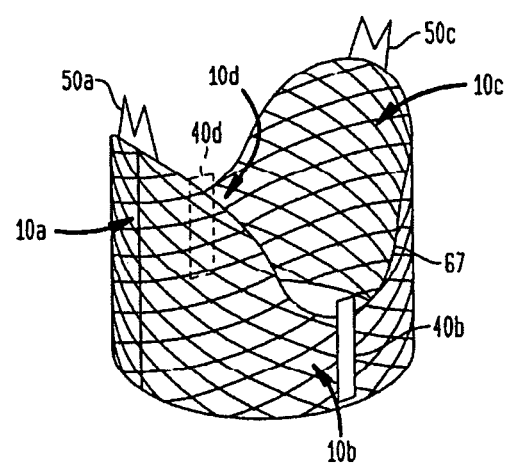
FIG. 19 is a diagrammatic perspective view of a stent in accordance with yet another embodiment of the present invention.
Figure 20:
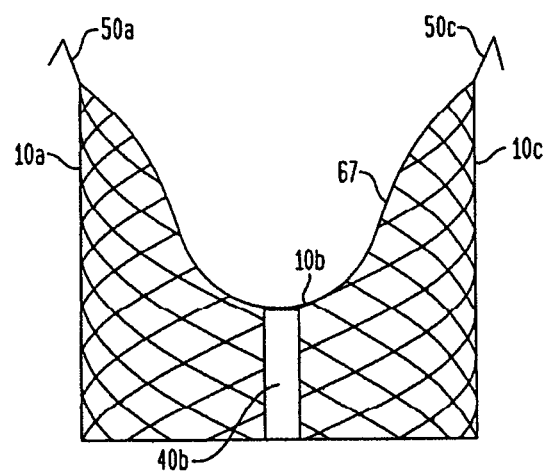
FIG. 20 is a diagrammatic elevational view of the stent shown in FIG. 19.

FIGS. 19 and 20 schematically depict a stent body design adapted for use in a bicuspid native valve. This design features an annular wall formed by a plurality of cells which may be similar to those discussed above. The annular wall has a scalloped top or distal edge 67 undulating in the proximal and distal directions around the circumference of the stent. This gives the stent four distinct quadrants 10*a*-*d*. The taller two quadrants, 10*a* and 10*c*, form projections which extend distally beyond the shorter quadrants or recess regions 10*b*, 10*d*. This stent body can be implanted, for example, in a bicuspid native valve, with the projections 10*a*, 10*c* aligned with the leaflets of the native valve. The projections provide additional radial outward force and surface area in order to efficiently displace the native leaflets and anchor the stent. The shorter two quadrants or recess regions 10*b* and 10*d* do not provide as much radial outward force, thereby reducing possible adverse effects on the native anatomy in these regions. The stent body may have commissure posts or other attachments for supporting prosthetic leaflets. For example, two commissure posts 40*b* and 40*d* are disposed in the recess regions 10*b* and 10*d*.

The stent body according to this embodiment has latch members 50*a* and 50*c* mounted on the projections 10*a* and 10*c* at or adjacent the distal ends of the projections. These latch members can engage the native leaflets in a manner similar to that discussed above. However, the projections may be employed even where latch members are not used.

Figure 21:
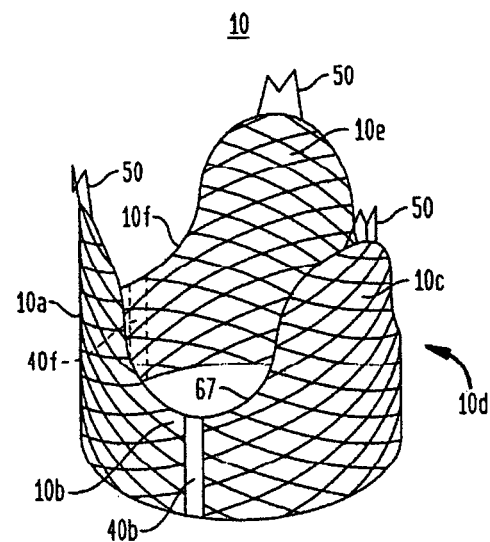
FIG. 21 is a diagrammatic perspective view of a stent in accordance with a still further embodiment of the present invention.
Figure 22:
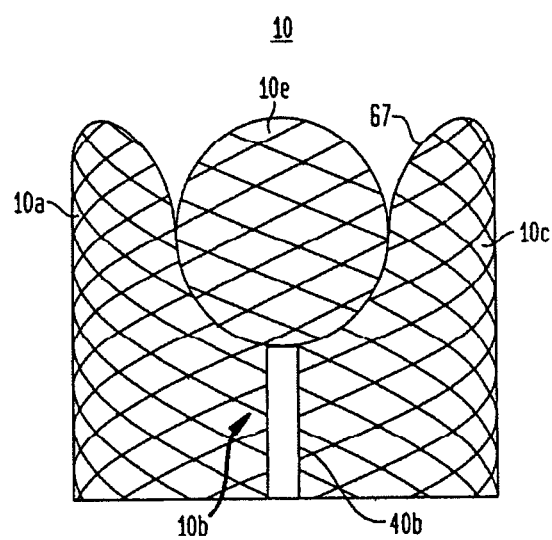
FIG. 22 is a diagrammatic elevational view of the stent shown in FIG. 17.

A tricuspid stent design depicted in FIGS. 21 and 22 has a scalloped tubular wall with an undulating distal edge 67 defining three projections, 10*a*, 10*c*, and 10*e*, and three recesses 10*b*, 10*d* and 10*f*. The projections and recesses are disposed in alternating sequence around the circumference of the stent body. Here again, the leaflet attachments or commissure posts 40 are disposed in the recesses 10*b*, 10*d* and 10*f*. A stent body according to this embodiment may be aligned with the calcified leaflets of a tricuspid native valve, providing additional radial outward force and surface area in order to efficiently displace the native leaflets and anchor the stent. The shorter three sections, 10*b*, 10*d*, and 10*f*, do not provide as much radial outward force, thereby reducing possible adverse effects on the native anatomy in these regions. This stent body also incorporates latch members at the distal ends of the projections.

Figure 23:
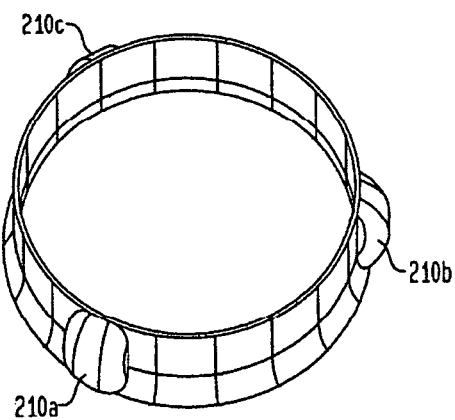
FIG. 23 is a perspective view of a cuff.

FIG. 23 shows a possible cuff design 200 for use with a stent body intended for installation in a tricuspid native valve as, for example, the stent body of FIGS. 21 and 22. The three bulge regions 210*a*-*c* of this cuff align with the three recess regions, 10*b*, 10*d*, and 10*f*, respectively, of the stent body in order to provide additional sealing, as well as additional axial anchoring. An alternative (not shown) is a cuff design having two bulges for use in a similar manner in a bicuspid native valve such as the stent shown in FIGS. 19 and 20. Cuffs having bulges and other features for promoting sealing engagement of the cuff and native valve anatomy are disclosed in commonly assigned U.S. Provisional Patent Application No. 61/134,995, ("the '995 Application) filed Jul. 15, 2008, the disclosure of which is hereby incorporated by reference herein, as well as in the co-pending, commonly assigned International Application claiming priority of the '995 Application, filed on even date herewith and naming Peter Nicholas Braido, Paul Edward Ashworth, and Julia Ann Neumann as inventors, the disclosure of which is also hereby incorporated by reference herein.

We turn now to some prosthetic valve leaflet designs and valve assembly features that can be used with the above stents.

Figure 24:
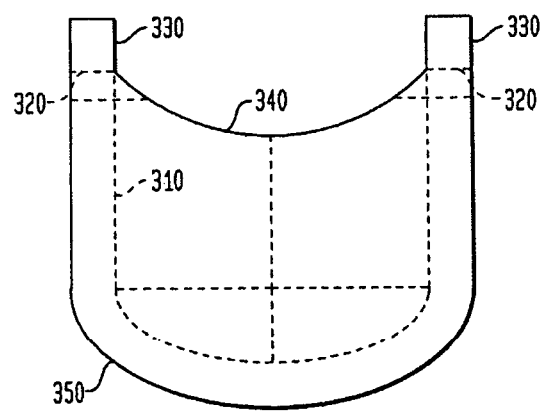
FIG. 24 is plan view of a prosthetic leaflet.

FIG. 24 is a flat, front view of a tricuspid prosthetic leaflet 300. Dashed lines 310 can be temporary patterns marked on the leaflet by means such as silk screening with surgical ink to allow for more accurate assembly and suturing. Areas 320 can be sutured to the most distal set of vertical eyelets 120 (e.g., FIG. 2) through the commissure posts 40 of the stent. Additional leaflet material 330 distal to the leaflet free edge 340 can be attached by sutures through the horizontal eyelets 130 (e.g., FIG. 2) in the commissure posts 140 of the stent. This can help to transfer the dynamic loading from the leaflet to the stent posts 40, instead of concentrating that load at high-stress area 320. Contoured leaflet belly 350 matches the stent scallop to more naturally mimic the native valve. Merely by way of example, the leaflet may be formed from an animal tissue such as bovine or porcine pericardium.

Figure 25:
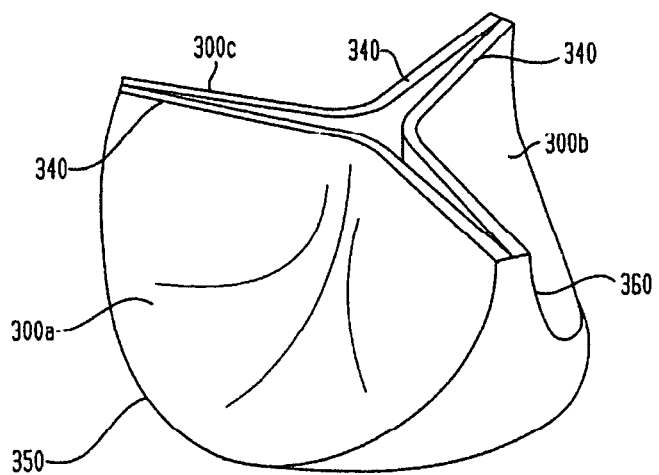
FIG. 25 is a diagrammatic perspective view of a leaflet assembly.
Figure 26:
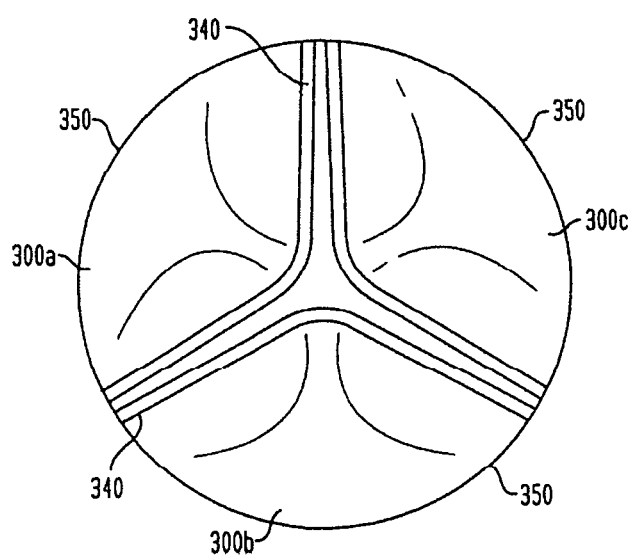
FIG. 26 is an end view of the leaflet assembly shown in FIG. 25.

FIGS. 25 and 26 are, respectively, perspective and axial views of a simplified tricuspid leaflet assembly formed from three instances of leaflets like leaflet 300 in FIG. 24. This assembly preferably provides additional areas of coaptation 360 between free edge regions of the leaflets. This helps ensure proper functioning of the prosthetic valve even in the event of malformation from the patient's anatomy. To amplify this point, leaflets 300 are shaped and assembled so that in addition to their free edges 340 coming together when the valve is closed, some additional material 360 of the leaflets upstream from free edges 340 can also come together when the valve is closed.

Figure 27:
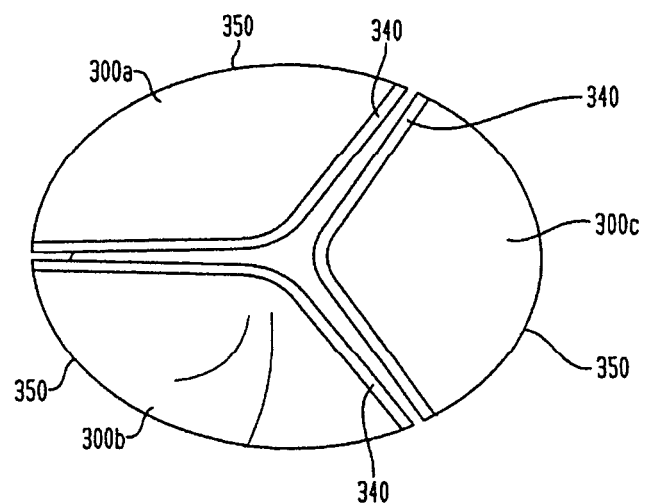
FIG. 27 is a diagrammatic perspective view of a further leaflet assembly according to a further embodiment of the invention.

FIG. 27 is an axial view of a tricuspid leaflet assembly having an elliptical shape. The leaflets here are intentionally elongated or shortened in specific directions to be assembled into a stent body having an annulus section with an elliptical cross-section. The stent body may be similar to that shown in FIG. 16, except that the stent body may have three commissure posts distributed around the circumference of the annulus section. A valve according to this embodiment of the invention may be implanted, for example, in a valve having an elliptical annulus as, for example a diseased mitral valve.

Figure 28:
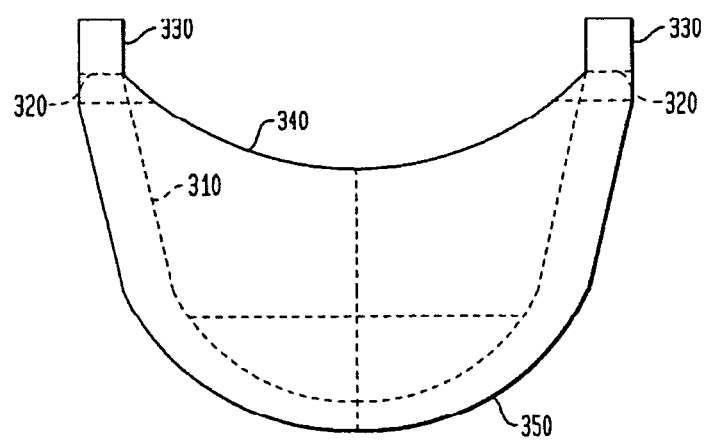
FIG. 28 is a plan view of a further prosthetic valve leaflet.

FIG. 28 is generally similar to FIG. 24. However, FIG. 28 shows a leaflet 300 for a bicuspid design. FIG. 28 has many of the same features as are described above in connection with FIG. 24, but the FIG. 28 design is elongated (left and right) to accommodate an elliptical shape with only two commissure posts for attachment.

Figure 29:
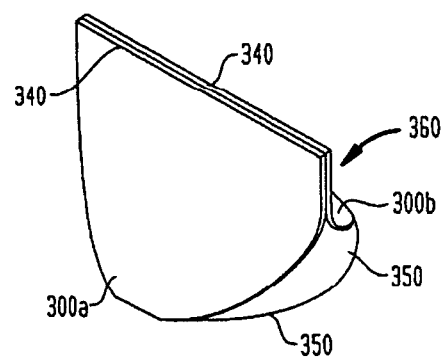
FIG. 29 is a diagrammatic perspective view of another leaflet assembly.

FIGS. 29 and 30 are, respectively, perspective and axial views of a simplified bicuspid leaflet assembly. Reference numeral 360 points to an additional area of coaptation between the leaflets when the prosthetic valve is closed. This helps ensure proper functioning of the prosthetic valve even if there is malformation of the valve from the patient's anatomy. Note that a bicuspid leaflet attachment can be assembled into a circular or elliptical stent.

Figure 31:
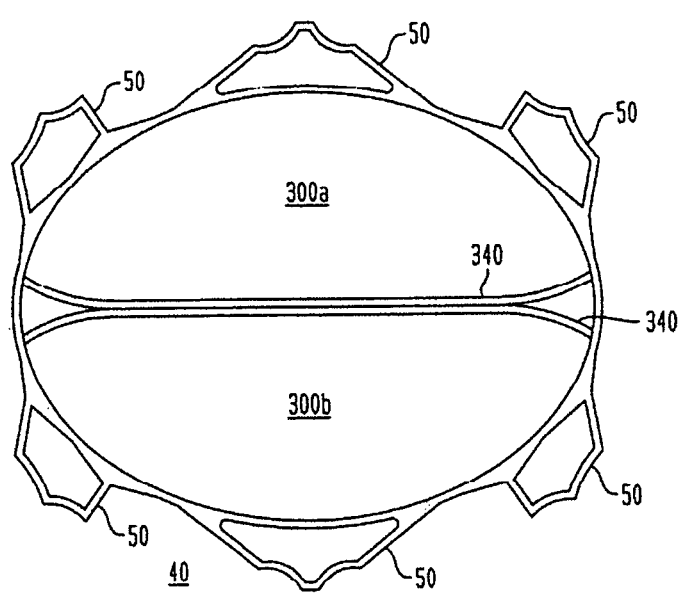
FIG. 31 is an end view of a valve in accordance with still another embodiment of the present invention.

FIG. 31 is a simplified top view of an elliptical, bicuspid, prosthetic valve design with six latches 50 evenly spaced around the valve. Either a bicuspid valve (as shown in FIG. 31) or a tricuspid valve can be intentionally pre-shaped to fit the leaflet (commissure) posts 40 into the native bicuspid commissures to ensure adequate sealing and anchoring. Elongated bicuspid leaflets 300a and 300b are shown in FIG. 31, as opposed to the typical Y-shaped coaptation of the three leaflets in a tricuspid valve. Again, it will be appreciated that a bicuspid leaflet attachment can be assembled into either a circular stent or an elliptical stent.

Figure 32:
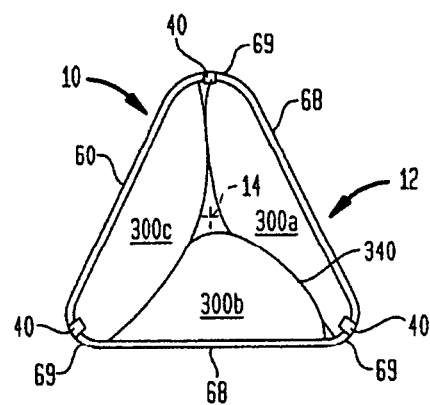
FIG. 32 is a diagrammatic end view of a valve according to a further embodiment of the invention.

A valve according to yet another embodiment of the present invention incorporates a stent body having an annulus section 12 (FIG. 32) with a generally tubular wall formed by a plurality of cells extending around the proximal-to-distal axis of the stent body. In the free or unconstrained configuration, the tubular wall has a generally triangular configuration as seen in cross-section in a plane perpendicular to the proximal-to-distal axis, as in FIG. 32. The wall thus has side regions 68 forming the sides of the cross-sectional shape and corner regions 69 connecting the side regions. The corner regions as seen in cross-section are generally arcuate. The valve is provided with three prosthetic leaflets 300a, 300b and 300c having coapting free edges 340. These free edges abut one another along commissures which extend into the corner regions 69. For example, the stent body may have commissure posts 40 disposed in the corner regions 69.

Figure 33:
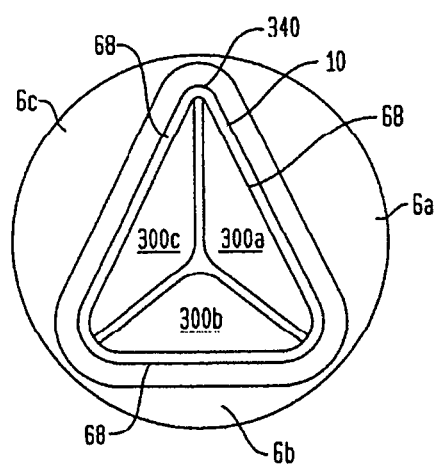
FIG. 33 is a diagrammatic end view of the valve of FIG. 32 invention in an installed condition, together with surrounding tissue.

When the valve is implanted in a native valve such as the aortic valve having three leaflets (FIG. 33), each of the three sides 68 of the stent body 10 may be adjacent (inside) a respective one of the patient's three native, stenotic, valve leaflets 6a-c. Each of three prosthetic valve leaflets 300a-c may then be inside stent body 10 adjacent a respective one of the native leaflets 6a-c. Here again, the stent body, when implanted, is in an expanded configuration, but is constrained by the native anatomy so that the stent body is not fully expanded to the unconstrained configuration. Thus, the resilient stent body bears on the native anatomy. A valve according to this aspect of the invention may be used, for example, where the native anatomy defines a generally triangular opening. For example, a stenotic native aortic valve defines such an opening. The stent body can provide adequate engagement force at the corner regions 69 without imposing excessive forces along the side regions 68.

A stent body and valve according to this embodiment may include the features discussed above. For example, the stent body may include latch members (not shown) along the distal edge of the annulus section as, for example, in the side regions 68. Also, the stent body may include an aortic section and support struts connecting the aortic section to the annulus section.

Numerous other variations and combinations of the features discussed above can be employed. For example, features as discussed in the various embodiments can be combined with one another. The cellular structure of the stents discussed above can be varied. For example, the features discussed above can be employed in woven stent bodies and in stent bodies which are not fully self-expanding as, for example, stent bodies which are forcibly expanded by a balloon or mechanical device during implantation. Also, the stent body need not include commissure posts. Other features can be used as attachments for prosthetic valve leaflets. Merely by way of example, the valve leaflets can be sutured directly to the cell struts as, for example, at intersections between cell struts, or to small metallic eyelets provided at such intersections or at other locations along the stent body.

Although the foregoing most frequently refers to prosthetic aortic valves, it will be appreciated that prosthetic valves in accordance with this invention can be used for other circulatory system valves (e.g., other valves in the heart). As just one example of this, elliptical prosthetic valves in accordance with the invention may be used as prosthetic mitral valves. Also, although the prosthetic valves have been described herein as being implanted in a naturally occurring native valve of the patient's circulatory system, the prosthetic valves described herein also can be implanted in a previously-implanted prosthetic valve. In the context of such a procedure, the previously-implanted prosthetic valve may be regarded as the "native" valve. In such a procedure the latch members of the stent body can engage leaflets of the previously-implanted prosthetic valve. In yet another variant, the latch members of the stent body may engage other features of the previously-implanted prosthetic valve. For example, the latch members may be engaged within cells of a stent body of the previously-implanted prosthetic valve. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A stent for use with a prosthetic heart valve for replacement of a native heart valve comprising an expandable non-woven stent body having a collapsed configuration and an expanded configuration, the stent body including an annulus section adjacent a proximal end of the stent, the annulus section including a plurality of closed cells arranged in a multiplicity of annular rows around a circumference of the stent body, the annulus section in the expanded configuration being generally tubular and adapted to engage the leaflets of the native heart valve and the annulus of the native heart valve with a proximal end of the annulus section adjacent the annulus of the native valve and a distal end of the annulus section adjacent distal ends of the native leaflets, the stent body including a plurality of latch members formed integrally with the annulus section, each of the latch members including a pair of connection struts and an engagement portion adapted to engage an exterior surface of a leaflet of the native valve, the connection struts being connected to the stent body at circumferentially-spaced locations in the annulus section and projecting distally from the locations to distal ends located distal to the annulus section, and the engagement portion being connected to the connection struts adjacent the distal ends thereof and projecting proximally from the distal ends of the connection struts to an engagement portion proximal end unconnected to other structure, each of the engagement portions being spaced from a next adjacent engagement portion around the circumference of the stent.

2. A stent as claimed in claim 1 wherein, in the expanded configuration, the engagement portion slopes outwardly in the proximal direction.

3. A stent as claimed in claim 1 wherein the engagement portion includes a pair of engagement struts connected to the connection struts adjacent the distal ends thereof and projecting proximally from the distal ends of the connection struts, the engagement struts being connected to one another adjacent proximal ends thereof.

4. A stent as claimed in claim 3 wherein the at least one row of expandable cells includes a plurality of interconnected cell struts joining one another at crests and defining the cells, the crests including a distal row of crests at the distal end of the annulus section, the connection struts being connected to the crests of the distal row.

5. A stent as claimed in claim 4 wherein the connection struts of the latch member are connected to the crests of the distal row that are not mutually adjacent to one another.

6. A stent as claimed in claim 3 wherein the engagement struts of the latch member project toward one another in circumferential directions.

7. A stent as claimed in claim 3 wherein the latch member includes a proximal end member extending between the proximal ends of the engagement struts.

8. A stent as claimed in claim 7 wherein the proximal end member is generally arcuate.

9. A stent as claimed in claim 8 wherein the proximal end member includes a bight projecting distally from the proximal ends of the engagement struts.

10. The stent of claim 1 wherein the annulus section includes a plurality of rows of the extendable cells.

11. The stent of claim 1 wherein the at least one latch member includes a plurality of the latch members circumferentially spaced around the annulus section.

12. The stent of claim 1 wherein the annulus section includes a plurality of commissure posts circumferentially spaced from one another.

13. A stent for use with a prosthetic heart valve for replacement of a native aortic valve, the stent comprising an expandable stent body having an expanded configuration including a generally tubular annulus section extending in proximal and distal directions, a generally tubular aorta section of larger diameter than the annulus section, the aorta section being spaced distally from the annulus section, and a plurality of support struts spaced circumferentially from one another and interconnecting the annulus section with the aorta section, the annulus section including a plurality of closed cells arranged in a multiplicity of annular rows around a circumference of the stent body, the stent body further including at least one latch member connected to the stent body adjacent the annulus section, the latch member including a pair of connection struts and an engagement portion disposed outward of the annulus section in the expanded configuration, the connection struts being connected to the stent body at circumferentially-spaced locations in the annulus section and projecting distally from the locations to distal ends located distal to the annulus section, and the engagement portion being connected to the connection struts adjacent the distal ends thereof and projecting proximally from the distal ends of the connection struts, the stent body being adapted for disposition with the annulus section adjacent the annulus of the native valve and at least partially within the leaflets of the native valve, the aortic section adjacent the native sinotubular junction and the support struts extending at least partially across the native Valsalva sinus, and with the engagement portion of at least one latch member engaged with at least one native valve leaflet.

14. The stent of claim 13 wherein the stent body is cut from a metal tube.

15. The stent of claim 13 wherein the annulus section includes a plurality of commissure posts spaced circumferentially from one another.

16. The stent of claim 15 wherein the plurality of support struts includes a group of support struts associated with each of the commissure posts, the support struts in the group being disposed circumferentially adjacent the commissure post associated with the group.

17. The stent of claim 16 wherein the latch member is offset circumferentially from the commissure posts and from the support struts.

18. The stent of claim 17 wherein the stent body has a collapsed configuration and wherein, in the collapsed configuration, the latch member extends distally from the annulus section between the support struts associated with different commissure posts.

19. The stent of claim 18 wherein the annulus section comprises one or more rows of expandable cells and the aorta section comprises one or more rows of expandable cells.

20. The stent of claim 13 including three of the latch members equally spaced circumferentially around the annulus section.

21. The stent of claim 20 wherein the annulus section includes three commissure posts equally spaced circumferentially around the annulus section alternating with the three latch members.

22. A valve comprising a stent as claimed in any of the preceding claims and a plurality of flexible prosthetic valve leaflets disposed at least partially within the annulus section when the stent is in the expanded configuration.

23. A method of treating a patient comprising implanting a valve as claimed in claim 22 in a native valve of the patient so that one or more leaflets of the native valve are engaged by the annulus section of the stent body and by one or more latch members of the stent body.

24. A stent for use with a prosthetic heart valve for replacement of a native valve, comprising:
  an expandable stent body having an expanded configuration including an annulus section having a plurality of cell struts joined to one another to form a plural number of closed cells cooperatively defining a generally tubular wall extending circumferentially around a proximal-to-distal axis, each of the cells having a distal cell crest, the distal cell crests of the cells in a most distal row of cells in the annulus section collectively defining a scalloped distal edge of the tubular wall including a number of circumferentially-spaced recess regions and a number of circumferentially-spaced projections extending distally beyond the recess regions, the projections being interspersed with the recess regions around the circumference of the tubular wall, each of the projections including a plurality of the distal cell crests and each of the recess regions including a plurality of the distal cell crests.

25. A valve comprising a stent as claimed in claim 24 and a plurality of flexible prosthetic valve leaflets having free edges and base edges, the leaflets being disposed at least partially within the annulus section when the stent is in the expanded configuration and being adapted to coapt with one another along the free edges, the free edges of the leaflets being connected to the annulus section at commissure locations circumferentially aligned with the recess regions of the wall.

\* \* \* \* \*